United States Patent [19]

Jones

[11] 4,001,246

[45] Jan. 4, 1977

[54] DERIVATIVES OF 24-METHYLENE-14A-AZA-D-HOMO-CHOLESTADIENES

[75] Inventor: Charles D. Jones, Indianapolis, Ind.

[73] Assignee: Eli Lilly and Company, Indianapolis, Ind.

[22] Filed: Jan. 19, 1976

[21] Appl. No.: 650,584

Related U.S. Application Data

[63] Continuation-in-part of Ser. No. 503,561, Sept. 6, 1974, abandoned.

[52] U.S. Cl. .................. 260/288 CF; 260/289 AZ; 260/287 AZ; 424/258; 195/12
[51] Int. Cl.² ............. C07D 215/16; C07D 215/38
[58] Field of Search ... 260/289 AZ, 289 C, 288 CF

[56] References Cited

UNITED STATES PATENTS

| | | | |
|---|---|---|---|
| 2,738,350 | 3/1956 | Mazur | 260/289 AZ X |
| 3,845,203 | 10/1974 | Williams et al. | 260/289 AZ X |

OTHER PUBLICATIONS

Tsuda et al., J. Am. Chem. Soc., 78, pp. 4107–4111 (1956).

*Primary Examiner*—Donald G. Daus
*Assistant Examiner*—D. B. Springer
*Attorney, Agent, or Firm*—Charles W. Ashbrook; Everet F. Smith

[57] ABSTRACT

Side chain oxidative modification of 24-methylene-14a-aza-D-homo-cholesta-8(9), 14(14a)-dienes provides novel steroid-like compounds which have antifungal activity.

6 Claims, No Drawings

DERIVATIVES OF 24-METHYLENE-14A-AZA-D-HOMO-CHOLESTADIENES

CROSS-REFERENCE TO RELATED APPLICATIONS

This application is a continuation-in-part of co-pending application Ser. No. 503,561, filed Sept. 6, 1974 now abandoned.

BACKGROUND OF THE INVENTION

Infections have fungal orgins constitute a large portion of human diseases caused by microorganisms. Several naturally occurring antibiotics and numerous synthetic compounds are currently available for treating fungal infections. Nystatin, a polyene antibiotic whose structural formula is not yet fully elucidated, is a commonly used antifungal agent which has met with good success. Even with the currently available antifungal agents however, there are still several diseases of fungal orgin which are not easily controlled. Additionally, certain antifungal agents become ineffective with continued use due to the patient's sensitization to the particular drug. Consequently, the search for new antifungal agents and the therapy of fungal infections is the object of much laboratory and clinical investigation.

The isolation and characterization of novel 24-methylene-14a-aza-D-homo-cholestadienes which show good antifungal activity has recently been accomplished from cultures of a strain of *Geotrichum flavobrunneum*. This organisms is described in detail by Miller et al., *Mycologia* 49, 779–808, 1957. The preparation and isolation of these novel steroid-like substances is the subject of U.S. Pat. No. 3,845,203.

The compounds provided by the present invention are in general prepared by modifying the side chain portion of the above-mentioned 24-methylene-14a-aza-D-homo-cholestadienes. The compounds provided herein are useful as antifungal agents.

SUMMARY OF THE INVENTION

The compounds of this invention have the formula

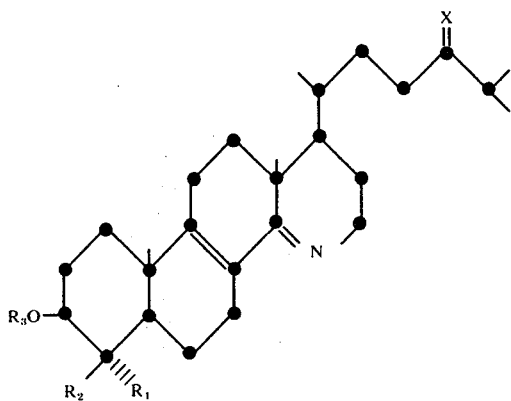

in which $R_1$ and $R_2$ are both hydrogen or both methyl; $R_3$ is hydrogen or $C_1$–$C_4$ alkanoyl; X is oxygen or $NOR_4$, in which $R_4$ is hydrogen, $C_1$–$C_4$ alkyl, or $C_1$–$C_4$ alkanoyl. The pharmaceutically acceptable salts of the organic bases having the above formula are included herein.

It is an object of this invention to provide new steroid-like compounds which are useful as antifungal agents.

DETAILED DESCRIPTION OF THE INVENTION

This invention relates to new organic ketones and oximes. More particularly, this invention relates to oxidation products of 24-methylene-14a-aza-D-homo-cholesta-8(9), 14(14a)-diene compounds.

As used herein, "$C_1$–$C_4$ alkanoyl" refers to carboxylic acid residues such as formyl, acetyl, propionyl, butyryl, isobutyryl, and the like. Examples of $C_1$–$C_4$ alkyl groups include methyl, ethyl, isopropyl, and related groups.

In general, the organic bases of this invention form pharmaceutically acceptable salts with any of a number of inorganic and strong organic acids. Whereas the particular acid used to form a salt is not critical, the salt that is formed should be substantially non-toxic to animal organisms. Acids commonly used in salt formation include sulfuric, hydrochloric, hydrobromic, phosphoric, sulfamic, lactic, acetic, maleic, succinic, benzoic, ascorbic, and related acids. The organic bases of the invention additionally form quaternary immonium salts with a variety of alkylating agents such as alkyl halides, alkyl sulfates, and sulfonates. Among such alkylating agents are methyl chloride, ethyl iodide, allyl bromide, methyl sulfate, methyl toluenesulfonate, and the like.

The compounds of this invention can be prepared by first oxidizing the exo-methylene group of a triene having the formula

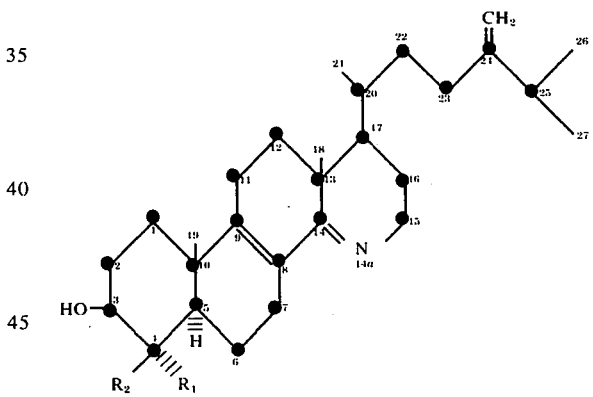

wherein $R_1$ and $R_2$ are both hydrogen or both methyl.

The compounds of the present invention are named systematically as cholestane derivatives by following the numbering system shown in the above formula. A preferred starting material, for example, is named accordingly as 3β-hydroxy-24-methylene-14a-aza-D-homo-5α-cholesta-8(9), 14(14a)-diene. It will be understood that all of the compounds provided herein will have the same basic stereochemical configuration as the starting material. For example, the compounds described hereinbelow will have a 3-hydroxy group, or a 3-alkanoyloxy group, in the β-configuration as indicated in the above formula by a solid bonding line between the carbon and oxygen atoms at $C_3$. Additionally, all of the compounds will have a hydrogen at $C_5$ in the α-configuration. By way of simplification, the terms α and β will be omitted from the systematic names used hereinafter in this application. For example, the preferred starting material named above will be hereinafter named as 3-hydroxy-24-methylene-14a-aza-D-homo-cholesta-8(9), 14(14a)-diene.

In one aspect of this invention, the 24-methylene-14a-aza-D-homo-steroid of the above formula is oxidized at the 24-methylene position to provide the corresponding 24-oxo derivative. Generally, the oxidation can be carried out with any of a number of commonly used oxidizing agents without affecting other reactive sites in the molecule. Examples of preferred oxidizing agents include ozone, osmium tetroxide in conjunction with sodium periodate or potassium permanganate, and the like. When ozone is selected as the oxidizing agent, only one molar equivalent should be used to insure that over-oxidation of the molecule does not occur. Preferably, the 24-methylene-14a-aza-D-homosteroid is treated with osmium tetroxide to convert the 24-methylene-group to what is believed to be the corresponding glycol, which generally is not isolated but is further oxidized by an oxidizing agent, such as sodium periodate or potassium permanganate for example, to the desired 24-oxo derivative. In practice, the 24-methylene starting material and osmium tetroxide are commingled in a suitable solvent. The amount of osmium tetroxide generally used for the oxidation ranges from about 0.01 to about 1.0 molar amount. Typical solvents commonly utilized include organic acids such as formic acid or acetic acid; ethers such as diethyl ether, dioxane, or diglyme; aromatics such as benzene or toluene; water; or mixtures of such solvents. The reaction is normally carried out at about 20° to 50° C., and the oxidation product that is formed after about 5 to 20 minutes generally is not isolated but is converted directly to the desired 24-oxo derivative by the addition of a suitable oxidizing agent, such as sodium periodate for example. Such an oxidizing agent is generally added directly to the reaction mixture in about a 2 to 20 molar amount. The oxidation of the glycol is normally complete after about 24 to about 100 hours when carried out at a temperature of about 20° to 30° C. The product, a 24-oxo-14a-aza-D-homocholestadiene, is isolated by removal of any excess oxidizing agents and any solvent, for example by filtration and evaporation, and further purification can normally be accomplished when desired by standard methods such as chromatography, crystallization, and the like.

The 24-oxo-14a-aza-D-homo-cholestadiene can be converted to the corresponding oxime by reaction with hydroxylamine. In particular, a 24-oxo derivative, such as 3-hydroxy-24-oxo-14a-aza-D-homo-cholesta-8(9), 14(14a)-diene for example, is treated with hydroxylamine in a suitable solvent, and generally in the presence of a base, to provide the corresponding 24-hydroxyimino derivative. The amount of hydroxylamine generally used is about one molar equivalent; however, more can be used if desired. The reaction is normally carried out in a solvent such as an alcohol, halogenated hydrocarbon, aromatic solvent, or water. Preferred solvents include ethanol, water, or pyridine. A base such as sodium hydroxide, sodium bicarbonate, triethylamine, pyridine, or the like, is generally added in amounts of about 1 molar equivalent or more. The reaction is generally complete after about 10 to 30 hours when carried out at a temperature of about 25° to 125° C. The product is usually isolated by removal of the solvent. Further purification can be accomplished if desired by chromatography, crystallization, or the like. The product can alternatively be isolated as the acid addition salt if desired by proper adjustment of the pH.

Like the 24-oxo-14a-aza-D-homo-cholestadiene derivatives, the oximes are useful as antifungal agents. Alternatively, the oximes can be converted to other useful compounds of the invention. In particular, the oxime can be alkylated, for example with an alkyl halide or an alkyl sulfate, to provide the corresponding oxime ether. In a typical preparation for example, an oxime derivative, prepared as described hereinabove, is treated with an alkylating agent, such as methyl sulfate or ethyl sulfate for instance, preferably in a solvent such as benzene, toluene, dichloromethane, diethyl ether, or the like. An acid binding agent such as triethylamine or pyridine can be incorporated in the reaction if desired. Generally, the reaction is carried out at about 25° to 80° C. and substantially complete after about 2 to 10 hours. The product is normally isolated by removal of excess solvent and alkylating agent, and further purification can be accomplished if desired by normal procedures such as chromatography or crystallization.

An alternative and preferred method of preparation of the alkylated oxime comprises condensing the 24-oxo-compound with an alkoxyamine, such as methoxyamine or ethoxyamine for instance. The reaction is carried out in a manner similar to that described hereinbefore for the oxime preparation.

The hydroxyimino derivatives can be acylated with a reactive derivative of an organic acid, such as an acid halide or an acid anhydride for example. The acylation reaction is generally carried out with an excess of acylating agent, for example a 2 to 10 molar excess, thereby acylating the $C_3$-hydroxy group in addition to the oximino group. The 3-alkanoyloxy can then be converted back to the 3-hydroxy group by mild basic hydrolysis, for example with 1 molar amount of aqueous sodium hydroxide or the like. Generally, the acylated oximino group is less susceptible to mild hydrolysis conditions.

Alternatively, the starting 3-hydroxy-24-oxo-14a-aza-D-homo-cholesta-8(9), 14(14a)-diene can first be acylated at the 3-hydroxy position, and the corresponding 3-alkanoyloxy derivative can subsequently be treated with hydroxylamine or an akloxyamine. More specifically, the $C_3$-hydroxyl group is simply acylated with an acylating agent, such as a $C_1$–$C_4$ alkanoyl halide or a $C_1$–$C_4$ alkanoic acid anhydride for instance. Typically, the 3-hydroxy derivative is commingled with about an equimolar amount or more of a suitable acylating agent, generally in the presence of a base such as pyridine or triethylamine for example. A solvent can be incorporated for the acylation if desired. Commonly used solvents include halogenated hydrocarbons such as benzene or toluene for example. A 3-alkanoyloxy steroid derivative of this invention can be easily converted to the 3-hydroxy derivative when desired, for example by alkaline hydrolysis with aqueous sodium hydroxide or the like.

The compounds of this invention are characterized as being 14a-aza-D-homo-cholestadienes. It should be noted that either or both of the two double bonds within the basic steroid polycarbocyclic system can be reduced if desired to provide additional new antifungal agents. Typical reductions are carried out with hydride reducing agents, such as sodium borohydride or lithium aluminum hydride for example, and with dissolving metals in liquid ammonia.

Illustrative examples of typical steroid-like compounds provided by this invention include, among others:

3-Hydroxy-24-oxo-14a-aza-D-homo-cholesta-8(9), 14(14a)-diene;

3-acetoxy-24-oxo-14a-aza-D-homo-cholesta-8(9), 14(14a)-diene;

3-Butyroxy-24-oxo-14a-aza-D-homo-4,4-dimethyl-cholesta-8(9), 14(14a)-diene;

3-Hydroxy-24-hydroxyimino-14a-aza-D-homo-cholesta-8(9), 14(14a)-diene;

3-Propionyloxy-24-methoxyimino-14a-aza-D-homo-cholesta-8(9), 14(14a)-diene-14a-ium chloride;

3-Hydroxy-24-butoxyimino-14a-aza-D-homo-4,4-dimethyl-cholesta-8(9), 14(14a)-diene-14a-ium acetate;

3-Isobutyroxy-24-methoxyimino-14a-aza-D-homo-cholesta-8(9), 14(14a)-diene-14a-ium bromide;

3-Hydroxy-24-oxo-14a-azonia-14a-methyl-D-homo-chloesta-8(9), 14(14a)-diene iodide;

3-Hydroxy-24-oxo-14a-aza-D-homo-4,4-dimethyl-cholesta-8(9), 14(14a)-diene;

3-Acetoxy-24-acetoxyimino-14a-aza-D-homo-cholesta-8(9), 14(14a)-diene;

3-Hydroxy-24-isobutyroxyimino-14a-aza-D-homo-cholesta-8(9), 14(14a)-diene; and the like.

As hereinbefore indicated, the starting materials required for preparing the compounds of this invention are 24-methylene-14a-aza-D-homo-cholesta-8(9), 14(14a)-diene derivatives. These triene substances are prepared by culturing the strain of *Geotrichum flavo-brunneum*, NRRL 3862, which strain is in the permanet culture collection of the Agricultural Research Service, Northern Utilization Research and Development Division, Department of Agriculture, Peoria, Ill. The organism which is cultured was isolated by the standard serial dilution procedure from a soil sample collected in the Grand Teton National Park region of Wyoming. The organism is described in detail by Miller et al., *Mycologia*, 49, 779-808, 1957. The preparation and isolation of the starting material used in the present invention is the subject of U.S. Pat. No. 3,845,203 and is carried out as described hereinbelow.

A culture of *Geotrichum flavo-brunneum* is grown under submerged aerobic conditions in a fermentation medium comprising carbohydrates, amino acids, and nutrient inorganic salts. The organism is grown for about 3 days at a temperature of about 20° to 35° C. After the fermentation is complete, the fermentation mycelium is extracted with a suitable organic solvent, such as ethyl acetate or amyl acetate for instance. Evaporation of the solvent from the combined organic extracts provides a mixture of compounds. The starting materials for the present invention are separated from the mixture by chromatography and crystallization.

The new compounds of the present invention are particularly useful because of their antifungal properties against microorganisms such as *Candida tripicalis*, *Candida albicans*, and *Trichophyton mentagraphytes*. The compounds provided by this invention have demonstrated useful in vitro antifungal activity when tested in standard disc plate assay employing fungal organisms such as *Candida albicans* and *Trichophyton mentagraphytes*. For example, 3hydroxy-24-oxo-14a-aza-D-homo-cholesta-8(9), 14(14a)-diene demonstrated a minimum inhibitory concentration (MIC) of 1.25 $\mu$g/ml. against *C. albicans* and 0.312 $\mu$g/ml. against *T. mentagraphytes*. Similarly, 3-hydroxy-24-hydroxyimino-14a-aza-D-homocholesta-8(9), 14(14a)-diene demonstrated an MIC of 1.25 $\mu$g/ml. against *C. albicans* and 0.625 $\mu$g/ml. against *T. mentagraphytes*.

The compounds provided herein can be admixed with suitable carriers and diluents and formulated as solutions or sprays for convenient administration to shower stalls, foot baths, and exterior surfaces of wood, brick, concrete, and other areas affected by fungal growth. Additionally, compounds of this invention can be applied to skin surfaces to combat fungal infection. The compounds can be formulated as ointments, creams, sprays, solutions and elixirs with suitable pharmaceutical carriers, diluents or excipients. Typical carriers, diluents and excipients commonly employed in such formulations include polyethylene glycol, propylene glycol, gelatin, hydrocarbon waxes, mannitol, glycerol, lanolin, and aqueous solutions such as saline solution, and water. An example of a typical formulation employing a compound of this invention comprises about 1 to 5 grams of a compound such as 3-acetoxy-24-oxo-14a-aza-D-homo-cholesta-8(9), 14(14a)-diene hydrochloride dissolved in about 1000 ml. of water. Such solution can be added to a typical foot bath or shower stall to combat fungal growth. Similarly, a compound such as 3-hydroxy-24-methoxyimino-14a-aza-D-homo-cholesta-8(9), 14(14a)-diene can be formulated by mixing about 250 mg. of such compound with about 250 mg. of mannitol and about 300 mg. of lanolin. Such mixture can be applied to a skin surface infected with a fungal growth at the rate of about 0.1 to 1 mg. of active ingredient per square centimeter of infected skin surface. As a further example, about 1 to 2 grams of 3-hydroxy-24-hydroxyimino-14a-aza-D-homo-cholesta-8(9), 14(14a)-diene can be dissolved in 500 ml. of ethanol and applied to a wood or concrete surface, or to a shower stall, in order to inhibit undesired fungal growth due to a microorganism such as *Candida albicans*.

The preparation of the compounds provided herein is more fully described in the following detailed preparations and examples. It is to be understood, however, that the examples are provided to serve only as illustration of particular aspects of the invention, and are not to be construed as limiting the invention to the particular compounds or methods specifically described. The compounds described hereinbelow are characterized by typical nuclear magnetic resonance (nmr) absorptions, given in delta ($\delta$) values, mass spectral (m/e) parent molecular ion absorption (M+), melting point, and by characteristic infrared absorptions.

PREPARATION 1

The production of the starting materials required for the present invention is illustrated by the following procedure.

Spores of *Geotrichum flavo-brunneum* strain NRRL 3862 were inoculated on a nutrient agar slant having the following composition:

| Agar Slant Medium | |
|---|---|
| Ingredient | Weight/Volume (g./l.) |
| Glucose | 20 |
| Peptone | 5 |
| Potassium Dihydrogen Phosphate | 0.5 |
| Magnesium Sulfate | 0.02 |
| Ferrous Sulfate | 0.01 |
| Agar | 20 |

The above culture were incubated at a temperature of 25° C. for 7 days. A loop of spores from the slant culture was transferred to a vegetative inoculum having the following composition:

| Vegetative Medium | |
|---|---|
| Ingredient | Weight/Volume (g./l.) |
| Sucrose | 25 |
| Edible Molasses | 36 |
| Corn Steep | 6 |
| Potassium Dihydrogen Phosphate | 2 |
| NZ Case[1] | 2 |
| Tap Water | |

[1]Enzymatic digest of casein, Scheffield Chemical Co., Norwich, N.Y.

The inoculated vegetative medium was shaken on a rotary shaker at 250 r.p.m. for about 24 to 48 hours at a temperature of about 25° C. Five percent of the volume of the vegetative inoculum containing viable vegetative growth was employed to inoculate a fermentation medium having the following composition:

| Fermentation Medium | |
|---|---|
| Ingredient | Weight/Volume (g./l.) |
| Glucose | 25 |
| Corn Starch | 10 |
| Peptone (meat) | 10 |
| NZ Amine A[1] | 4 |
| Molasses | 5 |
| Magnesium Sulfate Heptahydrate | 5 |
| Calcium Carbonate | 2 |
| Tap Water | |

[1]Pancreatic hydrolysate of casein, Scheffield Chemical Company, Norwich, N.Y.

The inoculated fermentation medium was agitated continuously for 72 hours at a temperature of 25° C. Throughout the fermentation, sterile air was passed through the fermentation medium at a rate of one half volume of air per volume of fermentation medium per minute.

Upon completion of the fermentation, the fermentation broth was extracted several times with ethyl acetate. The combined ethyl acetate extracts were concentrated to an oil residue. The residue was dissolved in a 20 percent acetone solution in n-hexane. Additional hexane was added to the mixture, and the solution was cooled to −20° C. whereupon 3-hydroxy-24-methylene-14a-aza-D-homo-cholesta8(9), 14(14a)-diene crystallized. The crystals were collected by filtration and air dried, m.p. 115°–118° C. The filtrate was concentrated to dryness, providing an oily residue which was dissolved in a mixture of ethyl acetate-hexane-distilled water (80:16:4). The solution was passed over a column packed with basic alumina (Wolem grade W200, Water Associates, Inc., Framingham, Mass.). The column was eluted with the same solvent mixture, and eluate fractions of 1 liter volume each were collected. Elutate fractions 9 through 23 were combined and the solvent was removed therefrom under reduced pressure to provide a residue which was crystallized from acetone. The crystals were collected by filtration and identified as 3-hydroxy-24-methylene-14a-aza-D-homo-4,4-dimethyl-cholesta-8(9), 14(14a)-diene, m.p. 147° C.

EXAMPLE 1

3-Hydroxy-24-oxo-14a-aza-D-homo-cholesta-8(9), 14(14a)-diene

A solution of 2 g. of 3-hydroxy-24-methylene-14a-aza-D-homo-cholesta-8(9), 14(14a)-diene in 80 cc. of 80 percent aqueous acetic acid solution was stirred at 25° C. while 25 mg. of oxmium tetroxide was added in one portion. The reaction mixture was stirred for five minutes, and 2.07 g. of sodium periodate was added to the reaction mixture. After stirring the reaction mixture at 25° C. for 72 hours, it was filtered and the solvent was removed from the filtrate, providing an oily residue. The residue was dissolved in 100 cc. of ethyl acetate and washed successively with aqueous sodium bicarbonate solution and with water, and dried. The solvent was removed under reduced pressure affording 1.5 g. of a crude product. The product was further purified by chromatography over a one inch by eight inch aluminum oxide column, eluting with ethyl acetate. The solvent was removed from the appropriate fractions affording 1.3 g. of 3-hydroxy-24-oxo-14a-aza-D-homo-cholesta-8(9), 14(14a)-diene as a crystalline solid. M.P. 70°–71° C., m/e: M$^+$ 413 nmr (CDCl$_3$):
  $\delta$1.02, 3H, C-18 CH$_3$
  $\delta$1.00, 3H, C-19 CH$_3$
  $\delta$0.91, 3H, C-21 CH$_3$
  $\delta$1.08, 6H, C-26,27 CH$_3$

EXAMPLE 2

3-Hydroxy-24-hydroxyimino-14a-aza-D-homo-cholesta-8(9), 14(14a)-diene

A solution of 1.4 g. of 3-hydroxy-24-oxo-14a-aza-D-homo-cholesta-8(9), 14(14a)-diene in 25 cc. of pyridine containing 1.3 g. of hydroxylamine hydrochloride was stirred and heated at 100° C. for 24 hours. The reaction mixture was concentrated to dryness under reduced pressure providing a residue which was dissolved in 100 cc. of ethyl acetate, washed with water and dried. The solvent was removed under reduced pressure affording 1 g. of 3-hydroxy-24-hydroxyimino-14a-aza-D-homo-choleata-8(9), 14(14a)-diene. m/e: M$^+$ 428. nmr (CDCl$_3$):
  $\delta$1.02, 3H, C-18 CH$_3$
  $\delta$0.96, 3H, C-19 CH$_3$
  $\beta$0.99, 3H, C-21 CH$_3$
  $\delta$1.08, 6H, C-26,27 CH$_3$

EXAMPLE 3

3-Acetoxy-24-oxo-14a-aza-D-homo-cholesta-8(9), 14(14a)-diene

A solution of 1 g. of 3-hydroxy-24-oxo-14a-aza-D-homo-cholesta-8(9), 14(14a)-diene in 10 ml. of acetic anhydride and 20 ml. of pyridine was stirred at 30° C. for 5 hours. Removal of the solvent by evaporation under reduced pressure provided an oil which was then dissolved in ethyl acetate and washed with water and dried. Evaporation of the solvent under reduced pressure then provided 3-acetoxy-24-oxo-14a-aza-D-homo-cholesta-8(9), 14(14a)-diene.

EXAMPLE 4

3-Hydroxy-24-methoxyimino-14a-aza-D-homo-cholesta-8(9), 14(14a)-diene

A solution of 1 g. of 3-hydroxy-24-oxo-14a-aza-D-homo-cholesta-8(9), 14(14a)-diene in 20 ml. of water and 10 ml. of dioxane was stirred at room temperature while 1 g. of methoxyamine hydrochloride was added to the reaction mixture in one portion. The reaction mixture was stirred at room temperature for 12 hours, and then poured into 50 ml. of ethyl acetate. The organic layer was separated, washed with water, and dried. Evaporation of the solvent under reduced pressure afforded 3-hydroxy-24-methoxyimino-14a-aza-D-homo-cholesta-8(9), 14(14a)-diene.

EXAMPLE 5

3-Acetoxy-24-acetoxyimino-14a-aza-D-homo-cholesta-8(9), 14(14a)-diene

To a solution of 3-hydroxy-24-hydroxyimino-14a-aza-D-homo-cholesta-8(9), 14(14a)-diene in pyridine was added an excess of acetic anhydride. The reaction mixture was stirred at room temperature for 6 hours and then concentrated to a small volume and poured into 50 ml. of ethyl acetate. The reaction mixture was then washed with water, dried, and the solvent was removed by evaporation under reduced pressure, providing 3-acetoxy-24-acetoxyimino-14a-aza-D-homo-cholesta-8(9), 14(14(14a)-diene.

I claim:

1. The compound of the formula

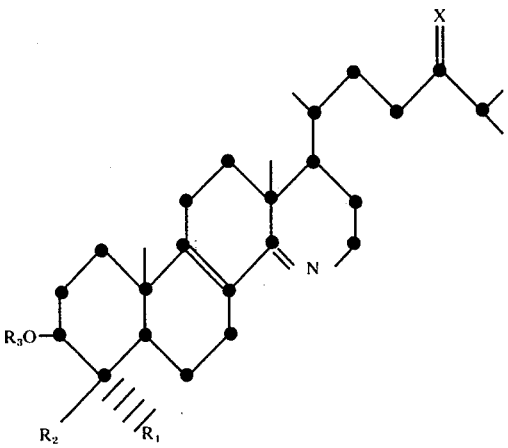

wherein:
$R_1$ and $R_2$ are both hydrogen or both methyl;
$R_3$ is hydrogen; and
X is oxygen or $NOR_4$, wherein $R_4$ is hydrogen or $C_1$–$C_4$ alkyl,;
and the pharmaceutically acceptable salts thereof.

2. The compound of claim 1 wherein $R_1$ and $R_2$ are both hydrogen.
3. The compound of claim 2 wherein $R_3$ is hydrogen.
4. The compound of claim 3 wherein X is oxygen.
5. The compound of claim 3 wherein X is $NOR_4$.
6. The compound of claim 5 wherein $R_4$ is hydrogen.

* * * * *